United States Patent [19]

Sato et al.

[11] Patent Number: 5,142,082
[45] Date of Patent: Aug. 25, 1992

[54] SILANE COMPOUND AND PROCESSES FOR THE PREPARATION THEREOF

[75] Inventors: Ryuji Sato; Satoshi Ueki; Tomoko Aoki, all of Saitama; Yoshiharu Okumura, Tokyo, all of Japan

[73] Assignee: Tonen Corporation, Tokyo, Japan

[21] Appl. No.: 787,234

[22] Filed: Nov. 4, 1991

[30] Foreign Application Priority Data

Nov. 16, 1990 [JP] Japan .................. 2-308519

[51] Int. Cl.⁵ ............................. C07F 7/18
[52] U.S. Cl. ................ 556/482; 556/469; 556/471
[58] Field of Search ............ 556/482, 469, 471; 572/471

[56] References Cited

U.S. PATENT DOCUMENTS

| | | | |
|---|---|---|---|
| 2,868,826 | 1/1959 | Bailey et al. | 556/482 |
| 2,974,157 | 3/1961 | Sex | 556/482 X |
| 3,542,838 | 11/1970 | Celsgaard | 556/482 |
| 4,956,484 | 9/1990 | Gerveuti et al. | 556/482 X |
| 4,958,041 | 9/1990 | Graefe et al. | 556/482 X |

Primary Examiner—Paul F. Shaver
Attorney, Agent, or Firm—Kane, Dalsimer, Sullivan, Kurucz, Levy, Eisele and Richard

[57] ABSTRACT

Novel silane compounds, tert.-butoxy cyclopentyl dimethoxysilane and isopropoxy cyclopentyl dimethoxysilane, are prepared by reacting cyclopentyl trihalosilane with ROH (where R stands for tert.-butyl or isopropyl group) and then with methanol, or by reacting cyclopentyl trimethoxysilane with ROH. The silane compounds are useful as a catlaytic component for olefin polymerization and as a silane coupling agent.

5 Claims, 4 Drawing Sheets

SILANE COMPOUND AND PROCESSES FOR THE PREPARATION THEREOF

FIELD OF THE INVENTION

This invention relates to a novel silane compound and processes for the preparation thereof, more specifically a novel silane compound which is suitable as a catalytic component for polymerization of olefin, particularly propylene, or as a silane coupling agent, and processes for the preparation thereof.

PRIOR ART

It is known that a polymer with high stereoregularity can be prepared by the use of alkoxy silanes as a catalytic component in the polymerization of propylene. However, it was impossible to sufficiently attain both high polymerization activity and high stereoregularity with known alkoxy silanes as a catalytic component in the polymerization of propylene.

Further, silane compounds are expected to be useful as silane coupling agents and resin modifiers. Accordingly, new silane compounds are awaited.

SUMMARY OF THE INVENTION

One object of the invention is to provide a novel silane compound.

Another object of the invention is to provide processes for the preparation of the novel silane compound.

The present invention provides a silane compound represented by the following formula (I):

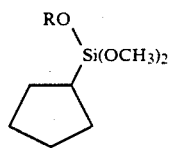
(I)

wherein R stands for a tert.-butyl or isopropyl group. Thus, the novel silane compound is tert.-butoxy cyclopentyl dimethoxysilane or isopropoxy cyclopentyl dimethoxysilane.

DETAILED DESCRIPTION OF THE INVENTION

Figure 1:
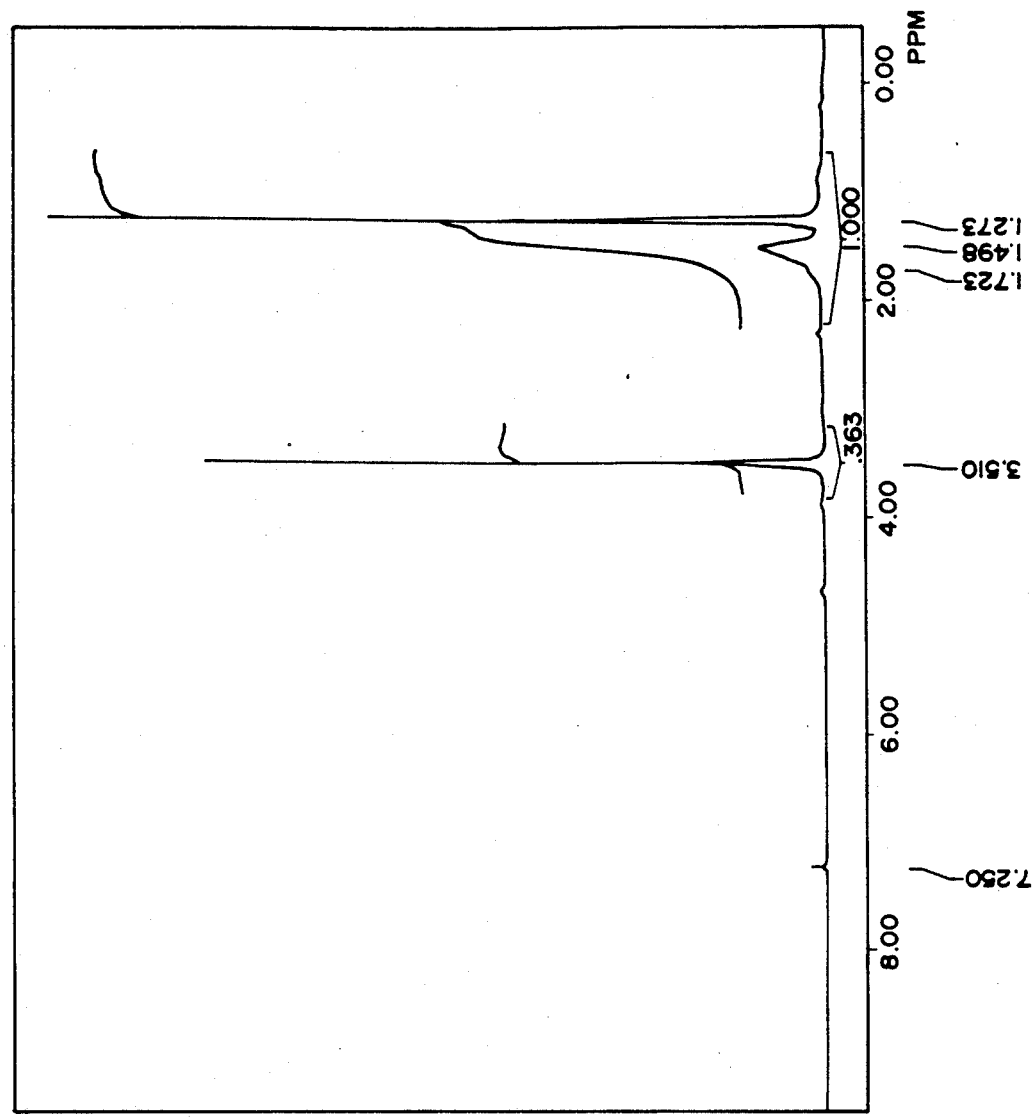
FIGS. 1 and 2 are charts of $^1$H-NMR and IR, respectively, of tert.-butoxy cyclopentyl dimethoxysilane prepared in Example 1.

The silane compound has a boiling point of 70° C./7 mmHg in the case where R is a tert.-butyl group; and 82° C./12 mmHg in the case where R is an isopropyl group. The structure of the silane compound may be confirmed by GC-MS, $^1$H-NMR, infrared absorption spectrum (IR) and so on.

When compound (I) in which R is a tert.-butyl group is analized by $^1$H-NMR, signals are observed at δ1.27 for the tert.-butoxy group, at δ1.4–1.8 for the cyclopentyl group and at δ3.51 for the methoxy groups. In the case where R is an isopropyl group, signals are observed at δ1.16, 1.26 and 3.9–4.6 for the isopropoxy group, at δ1.4–1.8 for the cyclopentyl group and at δ3.57 for the methoxy groups.

In analysis by IR spectra, a large absorption due to the SiOC bonds is observed around 1,100 cm$^{-1}$ in both compounds.

Olefinic polymers, such as polypropylene and polybutene, with high stereoregularity can be prepared at high polymerization activity using the silane compound (I) as a catalytic component.

As the silane compound (I) has hydrolytic groups, it can be used as a silane coupling agent, a polymerizable monomer and a resin modifier.

The invention also provides a process for the preparation of the novel silane compound represented by the aforesaid formula (I), wherein cyclopentyl trihalosilane is reacted with ROH, where R has the same meaning as defined above, and a resultant reaction product is reacted with methanol. The starting material, cyclopentyl trihalosilane is represented by the following formula (II):

where X stands for a halogen atom, preferably Cl or Br. It may easily be prepared from cyclopentene and trihalosilane, i.e., H-SiX$_3$ through hydrosilylation reaction:

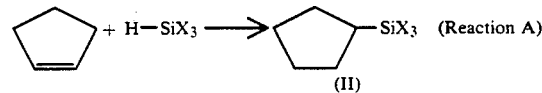
(Reaction A)

In the above reaction, 0.9 to 1.1 moles of trihalosilane may be used per mole of cyclopentene. The reaction is conducted in conditions of a temperature of 100° to 200° C. and 10 minutes to 10 hours, preferably with the use of a platinum catalyst such as platinum-1,1,3,3-tetramethyl-1,3-divinyldisiloxane complex. Solvents may also be used, such as benzene and toluene.

In the invention, the cyclopentyl trihalosilane (II) is reacted with ROH, i.e., tert.-butyl alcohol or isopropyl alcohol as follows:

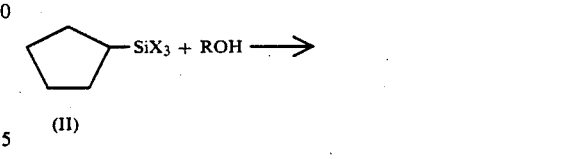
(Reaction B)

In the above reaction, 1 to 3 moles of ROH may be used per mole of cyclopentyl trihalosilane (II). The reaction may be carried out at a temperature of, for instance, 20° to 100° C. for 10 minutes to 5 hours, preferably at a temperature of 40° to 70° C. for 30 minutes to 2 hours. Solvents may be used, such as organic solvents, for instance, hexane, ethers, petroleum ether and benzene.

In the invention, it is preferred to use a hydrogen halide acceptor in the reaction mixture in order to facilitate the reaction. Examples of the hydrogen halide acceptor include tertiary amines, and nitrogen-containing heterocyclic compounds such as pyridine, quinoline and isoquinoline with pyridine and quinoline being preferred. 1 to 1.5 moles of the hydrogen halide acceptor are preferably used per mole of cyclopentyl trihalosilane.

The resultant reaction product (III) is then reacted with methanol according to the invention to prepare the silane compound (I) of the invention as follows:

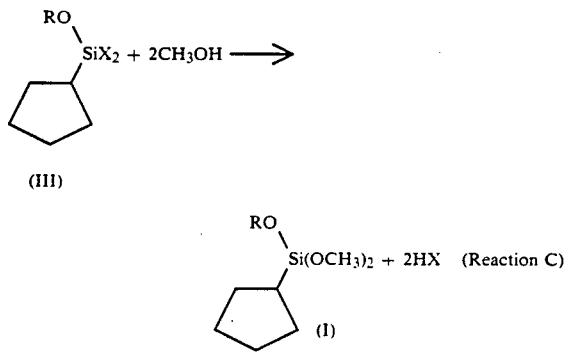

In the above reaction, 2 to 3 moles of methanol may be used per mole of the compound (III). The reaction may be carried out at a temperature of 0° to 100° C. for 10 minutes to 5 hours, preferably a temperature of 10° to 60° C. for 30 minutes to 2 hours. It is preferred to use a hydrogen halide acceptor also in Reaction C in order to facilitate the reaction. The hydrogen halide acceptors mentioned for Reaction B may be used also here. A hydrogen halide acceptors used here may be the same with or different from one used in Reaction B, but is generally the same as that. 2 to 3 moles of a halogen halide acceptor are preferably used per mole of the compound (III).

In the above reactions B and C, an inert gas may be blown in to remove formed hydrogen halide from the reaction system so as to facilitate the reactions.

The novel silane compound (I) may be prepared at high yield in the aforesaid process.

The invention also provide another process for the preparation of the silane compound represented by the formula (I), wherein cyclopentyl trimethoxysilane is reacted with ROH via exchange of alkoxy groups, where R has the same meaning as defined above.

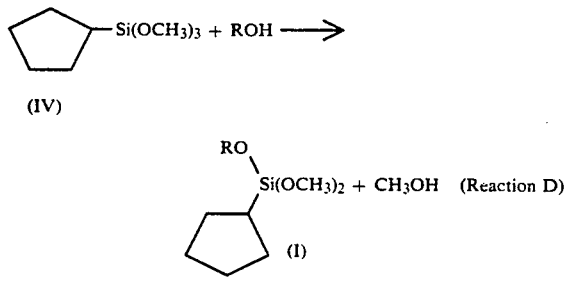

1 to 2 moles of ROH may be used per mole of the compound (IV). The reaction may be carried out at temperature of 50° to 100° C. for 2 to 20 hours. In this alkoxy groups exchange reaction, catalyst may be use such as acids, for instance, trifluoroborane-ether complexes and toluene sulfonic acid, or bases, for instance, alkali metal alkoxides and metal hydroxides.

The starting material, cyclopentyl trimethoxysilane (IV), may be prepared by reaction of cyclopentyl trichlorosilane with methanol to form hydrogen halide.

The invention will further be explained with reference to the following Examples, but the invention shall not be limited by the Examples.

EXAMPLE 1

Preparation of tert.-Butoxy Cyclopentyl Dimethoxysilane

In a 100 ml autoclave were charged 13.9 g (0.204 mole) of cyclopentene, 25.1 g (0.185 mole) of trichlorosilane and 25 μl of a 0.077 m mole/ml chloroplatinic acid solution in isopropyl alcohol (platinum content $1.92 \times 10^{-6}$ mole), which were then stirred at 150° C. for 30 minutes. Cyclopentyl trichlorosilane was obtained quantitatively.

In a 500 ml three-neck frask provided with a magnetic stirrer, a reflux condenser and a dropping funnel were charged the cyclopentyl trichlorosilane prepared above and 300 ml of hexane, to which a mixture of 49.3 g (0.623 mole) of pyridine and 20.1 g (0.271 mole) of tert.-butyl alcohol was added dropwise at room temperature under stirring.

After 2 hours reflux, 18.4 g (0.574 mole) of methanol were added and reflux was continued for further one hour and then the reaction was ended.

Figure 2:
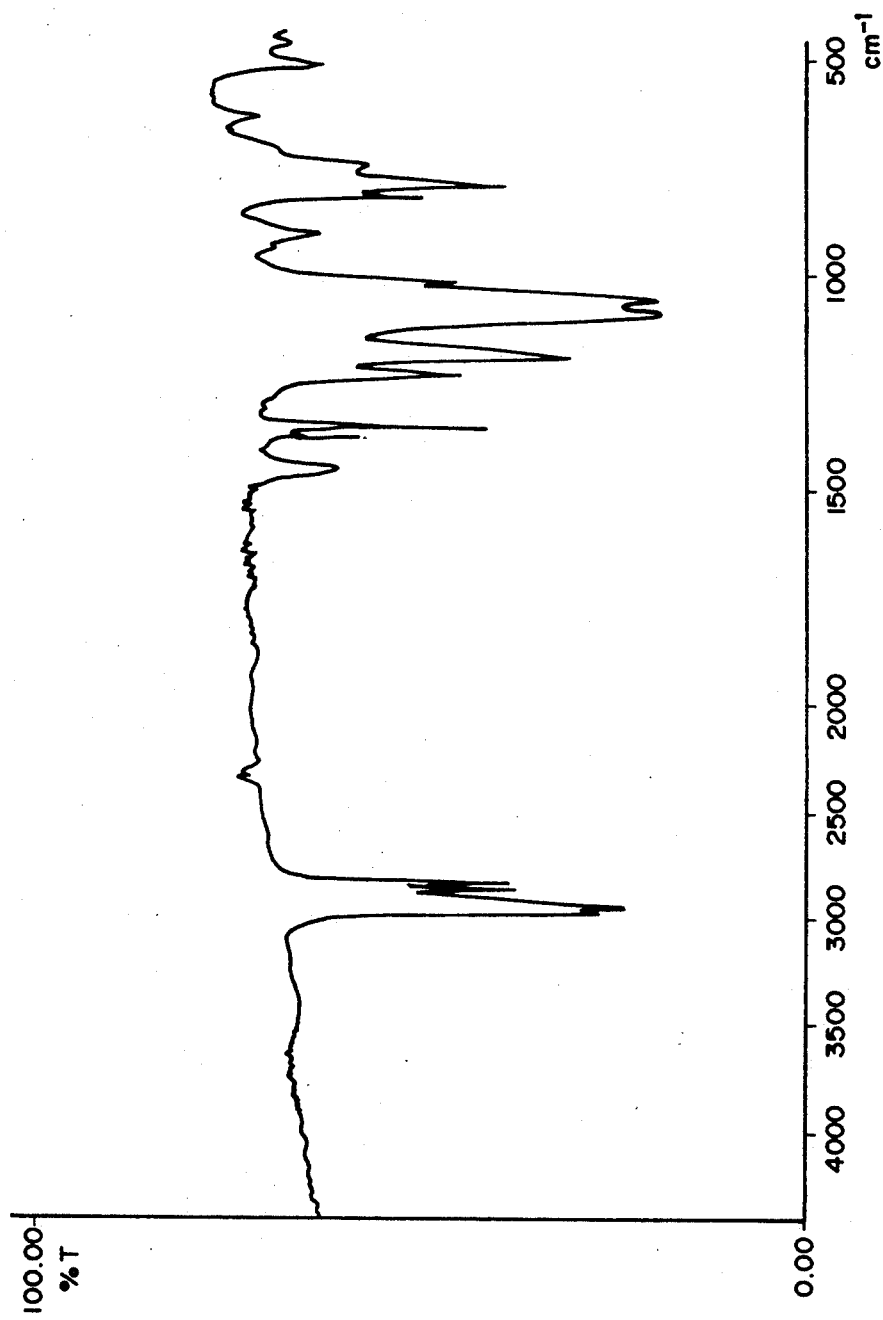

After a salt formed was filtered off and hexane was distilled off, a liquid of 32.7 g (0.141 mole) with a boiling point of 70° C./7 mmHg was obtained by vacuum distillation. This product was confirmed to be tert.-butoxy cyclopentyldimethoxysilane by GC-MS, $^1$H-NMR and IR. FIGS. 1 and 2 show the obtained results by $^1$H-NMR and IR, respectively. The yield was 76%.

The $^1$H-NMR and IR measurements were conducted in the following conditions.

$^1$H-NMR

Unit: HITACHI R-1500 (Hitachi Seisakusho)
Solvent: CDCl$_3$
Standard reference material: CHCl$_3$ and tetramethylsilane (TMS)

IR

Unit: 1600 Series FT-IR (Perkin Elmer)
Method: liquid film method (KBr plate)

For GC-MS measurement, HP 5970 B (Hewlett-Packard) was used. The measurement results, m/e vs. spectral intensity ratios in parentheses, are as follows: 217 (45), 175 (3); 163 (26), 131 (14), 107 (100), 77 (17) and 59 (7).

EXAMPLE 2

Another Preparation of tert.-Butoxy Cyclopentyl Dimethoxysilane

In a 100 ml three-neck flask provided with a magnetic stirrer and a reflux condenser were charged 25.0 g (0.131 mole) of cyclopentyl trimethoxysilane, 9.74 g (0.131 mole) of tert.-butyl alcohol and 20 mg (0.18 m mole) of potassium tert.-butoxide, which were then reacted with each other by heating under stirring in an oil both of 80° C. for 10 hours. After cooled, ammonium chloride was added to neutralize the alkali. Then, tert.-butoxy cyclopentyl dimethoxysilane of 6.25 g (0.0269 mole) was obtained by vacuum distillation. Its structure was confirmed as in Example 1. The yield was 21%.

EXAMPLE 3

Preparation of Isopropoxy Cyclopentyl Dimethoxysilane

In a 500 ml three-neck flask provided with a magnetic stirrer, a reflux condenser and a dropping funnel were charged 44.8 g (0.220 mole) cyclopentyl trichlorosilane prepared as in Example 1 and 320 ml of hexane, to which a mixture of 54.8 g (0.693 mole) of pyridine and 14.5 g (0.241 mole) of isopropyl alcohol was added dropwise at room temperature under stirring. After stirring for further 30 minutes, 15.5 g (0.484 mole) of methanol were added and the stirring was continued for further 30 minutes and then the reaction was ended.

Figure 3:
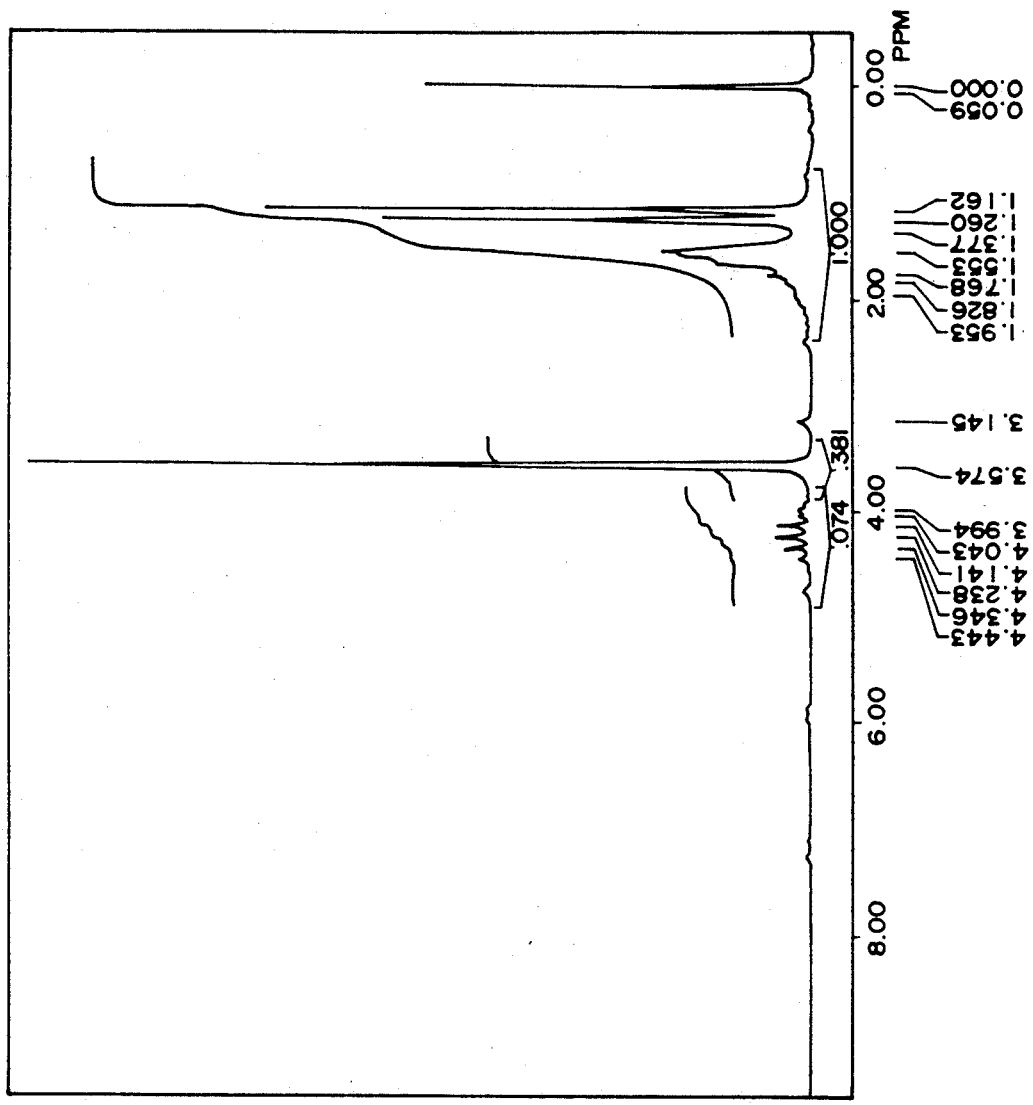
FIGS. 3 and 4 are charts of $^1$H-NMR and IR, respectively, of isopropoxy cyclopentyl dimethoxysilane prepared in Example 3.
Figure 4:
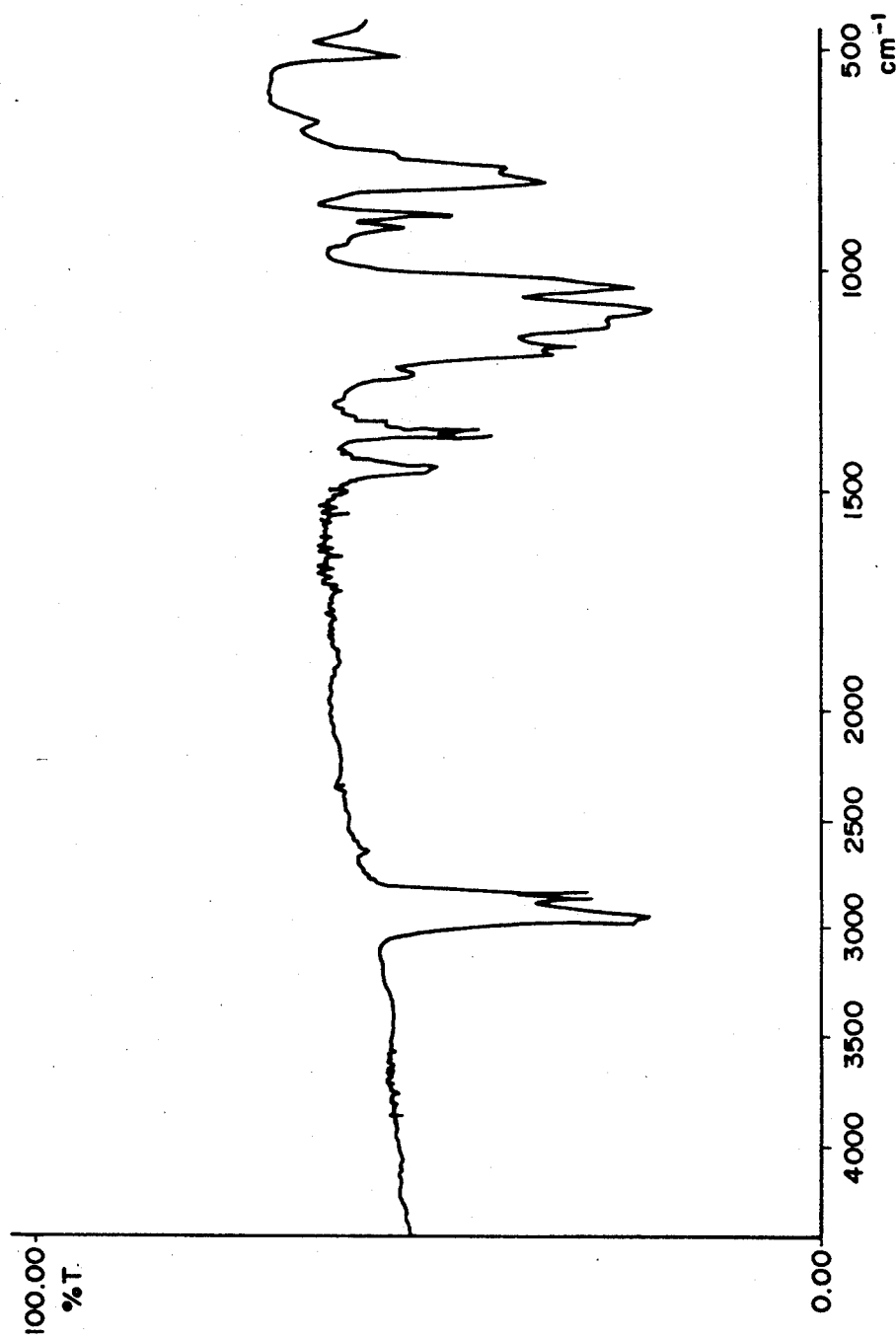

After a salt formed was filtered off and hexane was distilled off, a liquid of 30.7 g (0.141 mole) with a boiling point of 82° C./12 mmHg was obtained by vacuum distillation. This product was confirmed to be isopropoxy cyclopentyldimethoxysilane by GC-MS, $^1$H-NMR and IR. The measurement conditions were same as in Example 1 with the exception that TMS (tetramethylsilane) was used as a standard reference material in the $^1$H-NMR measurement. FIGS. 3 and 4 show the obtained results by $^1$H-NMR and IR, respectively. The yield was 64%.

The measurement results of GC-MS, m/e vs. spectral intensity ratio in parentheses, are as follows: 218 (1), 203 (5), 175 (2), 149 (74), 135 (20), 107 (100), 91 (19), 77 (39) and 59 (18).

EXAMPLE 4

Another Preparation of Isopropoxy Cyclopentyl Dimethoxysilane

In similar apparatus as used in Example 2 were charged 25.0 g (0.131 mole) of cyclopentyl trimethoxysilane, 7.87 g (0.131 mole) of isopropyl alcohol and 20 mg (0.18 m mole) of potassium tert.-butoxide.

Except the above, the procedure of Example 2 was repeated to obtain 5.15 g (0.0236 mole) of isopropoxy cyclopentyl dimethoxysilane. Its structure was confirmed as in Example 3. The yield was 18%.

What we claim is:

1. A silane compound represented by the following formula (I):

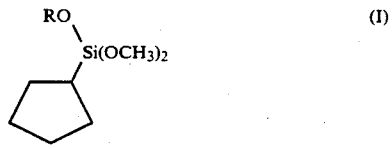

wherein R stands for a tert.-butyl or isopropyl group.

2. A process for the preparation of the silane compound represented by the above formula (I), characterized in that cyclopentyl trihalosilane is reacted with ROH, wherein R has the same meaning as in claim 1, and then a resultant reaction product is reacted with methanol.

3. The process as claimed in claim 2, wherein the reactions are conducted in the presence of a hydrogen halide acceptor.

4. The process as claimed in claim 3, wherein the hydrogen halide acceptor is a tertiary amine or a nitrogen-containing heterocyclic compound.

5. A process for the preparation of the silane compound represented by the above formula (I), characterized in that cyclopentyl trimethoxysilane is reacted with ROH via exchange of alkoxy groups, where R has the same meaning as in claim 1.